(12) United States Patent
Walton

(10) Patent No.: US 10,660,666 B2
(45) Date of Patent: May 26, 2020

(54) CUTTING TOOL

(71) Applicant: Steven William Walton, Bell Canyon, CA (US)

(72) Inventor: Steven William Walton, Bell Canyon, CA (US)

(*) Notice: Subject to any disclaimer, the term of this patent is extended or adjusted under 35 U.S.C. 154(b) by 208 days.

(21) Appl. No.: 16/034,154

(22) Filed: Jul. 12, 2018

(65) Prior Publication Data

US 2020/0015842 A1    Jan. 16, 2020

(51) Int. Cl.
*A61B 17/3207* (2006.01)
*A61B 17/00* (2006.01)
*A61B 17/32* (2006.01)

(52) U.S. Cl.
CPC ........ *A61B 17/320758* (2013.01); *A61B 2017/00017* (2013.01); *A61B 2017/00115* (2013.01); *A61B 2017/00398* (2013.01); *A61B 2017/320012* (2013.01); *A61B 2017/320052* (2013.01); *A61B 2217/005* (2013.01); *A61B 2217/007* (2013.01)

(58) Field of Classification Search
CPC .... A61B 17/320758; A61B 17/320725; A61B 17/320783; A61B 17/32002; A61B 2017/320775; A61B 17/32075
See application file for complete search history.

(56) References Cited

U.S. PATENT DOCUMENTS

| | | | |
|---|---|---|---|
| 5,258,007 A | | 11/1993 | Spetzler et al. |
| 5,993,467 A | * | 11/1999 | Yoon .................. A61B 17/0469 606/147 |
| 6,451,017 B1 | * | 9/2002 | Moutafis .......... A61B 17/32037 604/35 |
| 6,511,493 B1 | * | 1/2003 | Moutafis ........ A61B 17/320758 606/167 |
| 7,300,447 B2 | | 11/2007 | Eliachar et al. |
| 8,430,808 B2 | | 4/2013 | Piskun |
| 8,992,441 B2 | | 3/2015 | Vetter et al. |
| 9,055,967 B1 | | 6/2015 | Polo |
| 9,814,484 B2 | | 11/2017 | Schmitz et al. |
| 2002/0058944 A1 | * | 5/2002 | Michelson .......... A61B 17/1671 606/79 |
| 2004/0147934 A1 | | 7/2004 | Kiester |
| 2007/0261252 A1 | * | 11/2007 | Tu ........................ B23D 29/002 30/175 |
| 2009/0182361 A1 | * | 7/2009 | Thompson ..... A61B 17/320758 606/159 |
| 2009/0182362 A1 | * | 7/2009 | Thompson ..... A61B 17/320758 606/159 |

(Continued)

OTHER PUBLICATIONS

Eisenbeiss Inc., Parallel Co-Rotating Gear Systems https://www.eisenbeiss.com/gear-system/parallel-co-rotating-gear-systems/.

*Primary Examiner* — Katrina M Stransky
(74) *Attorney, Agent, or Firm* — Anooj Patel; Kevin Schraven; Hankin Patent Law, APC

(57) ABSTRACT

A cutting tool, comprising a motor; two rods, a first rod and a second rod; a synchronization gearing; and a cutter. The motor, synchronization gearing, and the two rods are operatively coupled such that when the motor turns the first rod, the synchronization gearing turns the second rod at the same speed in an opposite direction. The cutter is connected to both of the two rods, such that when the two rods spin in opposite directions the cutter rotates.

20 Claims, 10 Drawing Sheets

(56) References Cited

U.S. PATENT DOCUMENTS

| | | | |
|---|---|---|---|
| 2009/0318942 A1* | 12/2009 | Shturman | A61B 17/320725 |
| | | | 606/159 |
| 2009/0326568 A1* | 12/2009 | Shturman | A61B 17/320725 |
| | | | 606/159 |
| 2010/0010492 A1* | 1/2010 | Lockard | A61B 17/221 |
| | | | 606/79 |
| 2010/0063353 A1 | 3/2010 | Eliachar et al. | |
| 2011/0306995 A1* | 12/2011 | Moberg | A61B 17/320783 |
| | | | 606/159 |
| 2011/0307001 A1 | 12/2011 | Becker | |
| 2011/0313316 A1* | 12/2011 | Ranpura | A61B 10/0275 |
| | | | 600/566 |
| 2014/0100558 A1* | 4/2014 | Schmitz | A61B 17/3478 |
| | | | 606/33 |
| 2015/0196320 A1* | 7/2015 | Robinson | A61B 17/320758 |
| | | | 606/159 |
| 2017/0273698 A1* | 9/2017 | McGuckin, Jr. | |
| | | | A61B 17/00234 |
| 2017/0290603 A1* | 10/2017 | Piippo Svendsen | |
| | | | A61B 17/320758 |
| 2017/0333076 A1* | 11/2017 | Bruzzi | A61B 17/320725 |
| 2017/0348018 A1* | 12/2017 | Chanduszko | A61B 17/320725 |
| 2018/0042640 A1* | 2/2018 | Govari | A61B 17/320758 |
| 2018/0042641 A1* | 2/2018 | Govari | A61B 17/320758 |
| 2018/0235652 A1* | 8/2018 | Benjamin | A61B 17/320725 |
| 2020/0046403 A1* | 2/2020 | Piippo Svendsen | |
| | | | A61B 17/32002 |

* cited by examiner

CUTTING TOOL

FIELD OF USE

The present disclosure relates generally to systems and devices for cutting, and more specifically, to devices, methods, and systems for cutting soft tissue of a body in a medical setting.

BACKGROUND

Surgeons need a precise cutting tool that is able to reach deep into the interior of a body, such as a knee joint. This requires a tool that might need to be five inches (5") in length or more. But the cutting tool must also be thin enough to fit into a very small incision, such as a quarter of an inch (¼"), and must also be flexible so that only the soft tissue, and not bone, is cut by the cutting tool. Before the cutting tool of the present disclosure, the tools of choice to make medical cuts were scalpels and rotary systems. But these systems are very aggressive and all take a long time to access the cutting area. Additionally, they require great delicacy and a deft touch in order not to not to damage the surrounding body elements.

Therefore, there is a need for a device, system, and/or method for cutting soft tissue deep within the interior of the body without cutting or causing damage to the bone or other surrounding body elements.

SUMMARY OF EMBODIMENTS

To minimize the limitations in the prior art, the present specification discloses a new and useful device, system, and method for cutting the soft tissue of a body without damaging or cutting any nearby bones.

In one embodiment, the cutting tool of the present disclosure may be a miniature cutting system that is used to remove soft tissue (cartilage, fat, connective tissue, scar tissue) in areas of the body where access is difficult, such as the interior of the joints.

One embodiment of the cutting tool may be an abrasive wire, such as a wire with a rough surface, a wire with inserted pins, or the like. The wire may be connected to a tube, that spins around and turns the wire into a thin and precise cutting tool that can be inserted deep within a joint without fear of cutting the any nearby bones.

In one embodiment the cutting tool itself is long and thin but may have a wide cutting surface. The active cutter may be made from a thin wire, such as one that is 0.093" O.D. and ½" long. This wire may rotate around its own axis. This creates a large cutting surface with a very narrow profile.

In one embodiment, the cutting tool may have a laser pointer that shows the area that will be cut away and/or removed.

In another embodiment, the cutting tool of the present disclosure may be an ergonomically shaped hand-held unit that can be powered by battery, corded electricity, pneumatics, and the like. There may be an on/off and/or speed control engagement portion (digital or analog), which may be referred to as a speed controller. The speed controller may control a high-speed motor, which may be connected with two parallel rods, which are thin and spin at the same speed but opposite directions. There may also be a laser that points to the areas that will be cut by the cutter, which may be made from a thin abrasive wire connected to the stainless rods, directly or through a plastic tube. When the motor is activated at high speed revolutions per minute, (rpm) the rods will rotate at the same speed as the motor. The wire, in mechanical connection with the rods will rotate also, around its own axis. This high-speed rotation will make the surface of the wire work as a very abrasive cutting tool and it can be used to remove or cut soft tissue. The wire is preferably not so hard that it is able to cut bone.

In one embodiment, the device may also have an extraction hose that may be attached to the device to suck up cut off debris tissue. The cutting tool may also comprise a saline delivery system that can be used to wash the area while cutting.

Another embodiment may be a medical cutting tool that comprises two parallel counter-rotating rods, connected on their distal end by a flexible neoprene tube/rod. The neoprene tube/rod may have one or more wires or stainless-steel pins embedded within the tube/rod, such that as the parallel counter-rotating rods rotate, the neoprene tube/rod also rotates, thereby causing the stainless-steel pin(s) or wire(s) to rotate on the axis, which may then be used to be able to cut through tissue. Additionally, at higher speeds, the stainless-steel pin(s) may be able to cut through tougher material, such as bone. In order to avoid damaging bone, the user may select a flexible wire to be the cutter. Neoprene may be used as the tube connector because other materials may not be as suitable for high rotation speeds. The stainless-steel pins may also have a lip or protrusion, so that the stainless-steel pins do not become dislodged during use. The cutting tool may also comprise an extraction hose to remove cut off debris, and a laser guide to visually indicate the tissue to be cut. Preferably, the device may reach speeds of approximately 25,000 rpm or more.

One embodiment of the cutting tool may comprise: a motor; two rods, a first rod and a second rod; a synchronization gearing; and a cutter; wherein the motor turns the first rod in a first direction; wherein the synchronization gearing is operatively coupled to the first rod and the second rod, such that when the motor turns the first rod in the first direction, the second rod is turned in an opposite direction but at the same speed as the first rod; wherein the cutter is connected to both of the two rods, such that when the two rods spin in opposite directions the cutter rotates. The cutting tool may further comprise a drive shaft; wherein the synchronization gearing may comprise a first synchronization gear and a second synchronization gear; wherein the motor may be connected to and drive the drive shaft; wherein the first rod may comprise a rod gear and may be connected to the first synchronization gear; wherein the second synchronization gear may be connected to the second rod; wherein the drive shaft may comprise a rod engagement gear, which may engage with the rod gear, such that when the drive shaft turns the first rod and the first synchronization gear may turn; wherein the first synchronization gear and the second synchronization gear may be configured to engage, such that when the first rod turns, the second rod turns at the same speed in an opposite direction. The cutter may comprise a flexible portion and an active cutting portion. The active cutting portion may be a wire, a pin, or a plurality of pins. If it is a wire, the wire may prevent the cutting tool from damaging bone. The cutter may further comprise two rod tips; wherein the two rod tips are configured to removeably connect to the two rods, such that the cutter may be removeably connected to the cutting tool. The cutting tool may further comprise at least one or more of the following: a light; a LED light; a laser; a camera; a rinse; and a suction. The cutting tool may also have a speed controller; wherein the speed controller is configured to adjust a speed of the cutting tool.

It is an object to overcome the deficiencies of the prior art.

These, as well as other components, steps, features, objects, benefits, and advantages, will now become clear from a review of the following detailed description of illustrative embodiments, of the accompanying drawings, and of the claims.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps, which are illustrated. When the same numeral appears in different drawings, it refers to the same or like components or steps.

DETAILED DESCRIPTION OF THE DRAWINGS

In the following detailed description, numerous specific details are set forth in order to provide a thorough understanding of various aspects of one or more embodiments. However, these embodiments may be practiced without some or all of these specific details. In other instances, well-known methods, procedures, and/or components have not been described in detail so as not to unnecessarily obscure aspects of embodiments.

While multiple embodiments are disclosed, still other embodiments will become apparent to those skilled in the art from the following detailed description. As will be realized, these embodiments are capable of modifications in various obvious aspects, all without departing from the spirit and scope of protection. Accordingly, the screen shots, figures, and the detailed descriptions thereof, are to be regarded as illustrative in nature and not restrictive. Also, the reference or non-reference to a particular embodiment shall not be interpreted to limit the scope of protection.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 15% of the indicated number or range of numbers. In one embodiment, the term "approximately" and "about", refer to a deviance of between 0.0001-40% from the indicated number or range of numbers.

Figure 1:
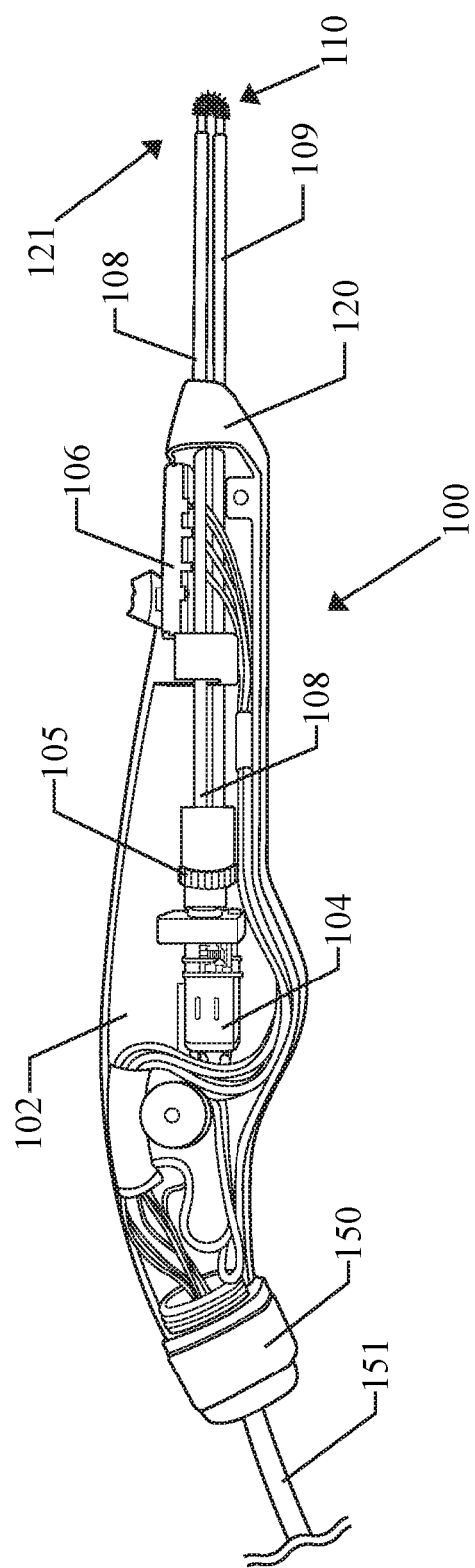
FIG. 1 is an illustration of a perspective side view of one embodiment of a cutting tool.

FIG. 1 is an illustration of a perspective side view of one embodiment of a cutting tool. FIG. 1 shows that the cutting tool 100 may comprise a housing 102, a motor 104, a synchronization gearing 105, motor speed controller 106, rods 108, 109, cutter 110, rod stabilizer 120, power supply (not shown), cord grip 150, cord 151. As shown, the motor 104, which preferably may be an electric or pneumatic motor, is coupled to the two rods 108, 109, such that the motor 104 rotates both rods 108, 109 simultaneously. Preferably, the rods 108, 109 turn at exactly the same speed in a synchronized manner, but they turn or spin in opposite directions. The synchronization gearing 105 may be coupled to both the rods and the motor 104 to ensure that the rods 108, 109 turn in opposition directions and at the same speed in a synchronized manner. Although the housing 102, which protects the internal components of the cutting tool 100, is shown as transparent, in order to display the internal components, it may also be opaque. The motor 102 may be powered by a power supply (not shown), which may be a battery or an alternating current that is supplied by a cord 151, or quick coupling connector. Alternatively, the electric motor may be a pneumatic motor that is driven by the expansion of compressed air. Preferably, the user may control the speed of the motor and/or the rotational speed of the rods 108. This may be done by including a speed controller 106, which may be a potentiometer, such as a linear potentiometer. The motor 102 and speed controller 106 may be operatively coupled to each other and may be controlled via a digital or analog controller, shown in FIG. 2. The motor 102 may be a high-speed motor that may turn at between approximately 2000 to 40,000 revolutions per minute (rpm). Preferably the speeds may vary from 8000 to 25,000 rpms. Additionally, the torque applied to the rods 108, 109 may be variable to limit the amount of force applied for cutting, thereby preventing unintended cutting. For example, where a soft tissue is to be cut, a low amount of torque may be applied to the rods 108, 109 so that if the cutter 110 were to come into contact with bone, for example, the cutter 110 would be unable to cut the bone, thereby limiting damage to unintended portions.

FIG. 1 shows that the rods 108, 109 may extend substantially from motor 102, out of the rod stabilizer 120 to a distal end 121. The length of the rods 108, 109 may vary from 0.2 inches to 10 inches. Preferably the length is at least 3 to 6 inches, in order to allow the cutter 110 to move deep within a body portion, such as a joint. The rods 108, 109 as shown may be long and thin so that they can fit through a very small incision in the patient's skin, such as 1/16 to 1/2 inches. At the distal end 121 of the rods 108, 109 is the cutter 110. The rods 108, 109 are preferably stainless-steel, so that they may be precisely engineered and very strong. Other materials, such as composites or aluminum may be used, so long as the appropriate precision and strength is achieved.

Figure 2:
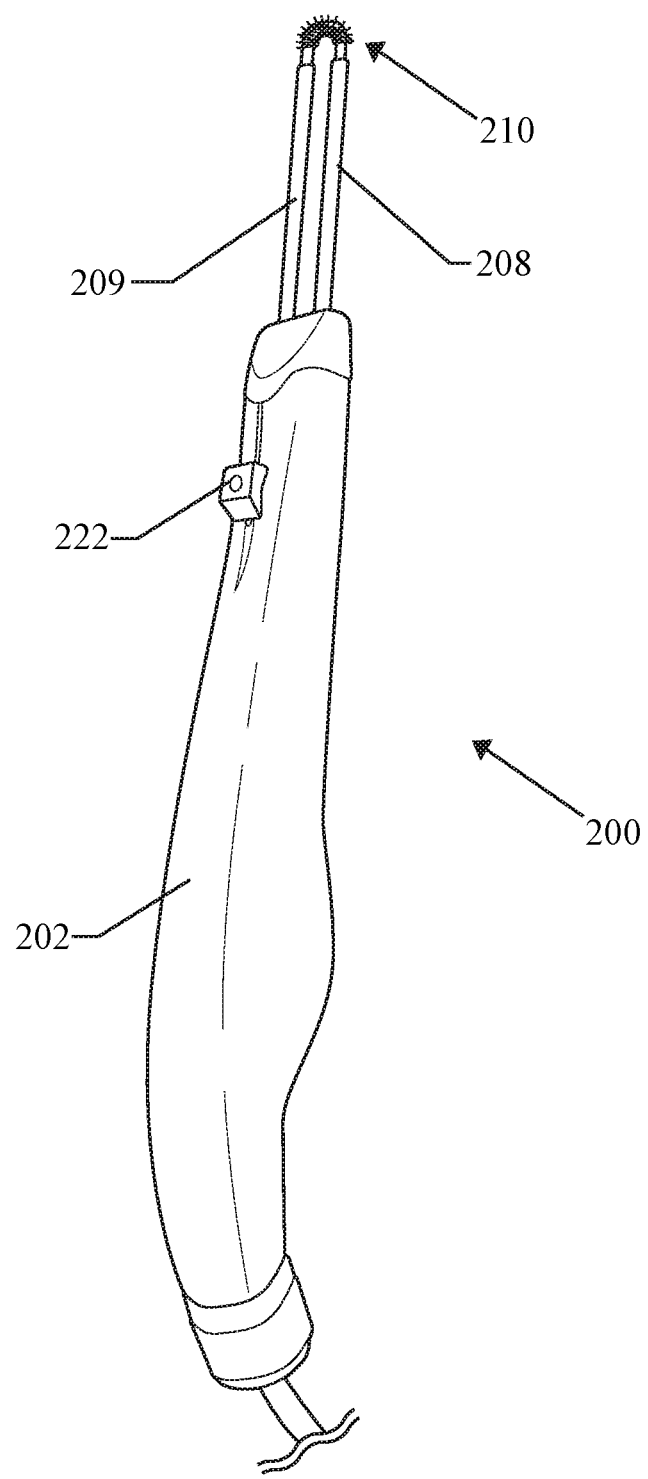
FIG. 2 is an illustration of a perspective rear view of one embodiment of a cutting tool.

FIG. 2 is an illustration of a perspective rear view of one embodiment of a cutting tool. FIG. 2 shows that cutting tool 200 may have a compact and ergonomic design and may comprise a housing 202, speed control button 222, rods 208, 209, and cutter 210. The speed control button 222 is shown as an analog switch, but may be a digital interface. There also may be a separate power on/off button that may be digital or analog.

Figure 3:
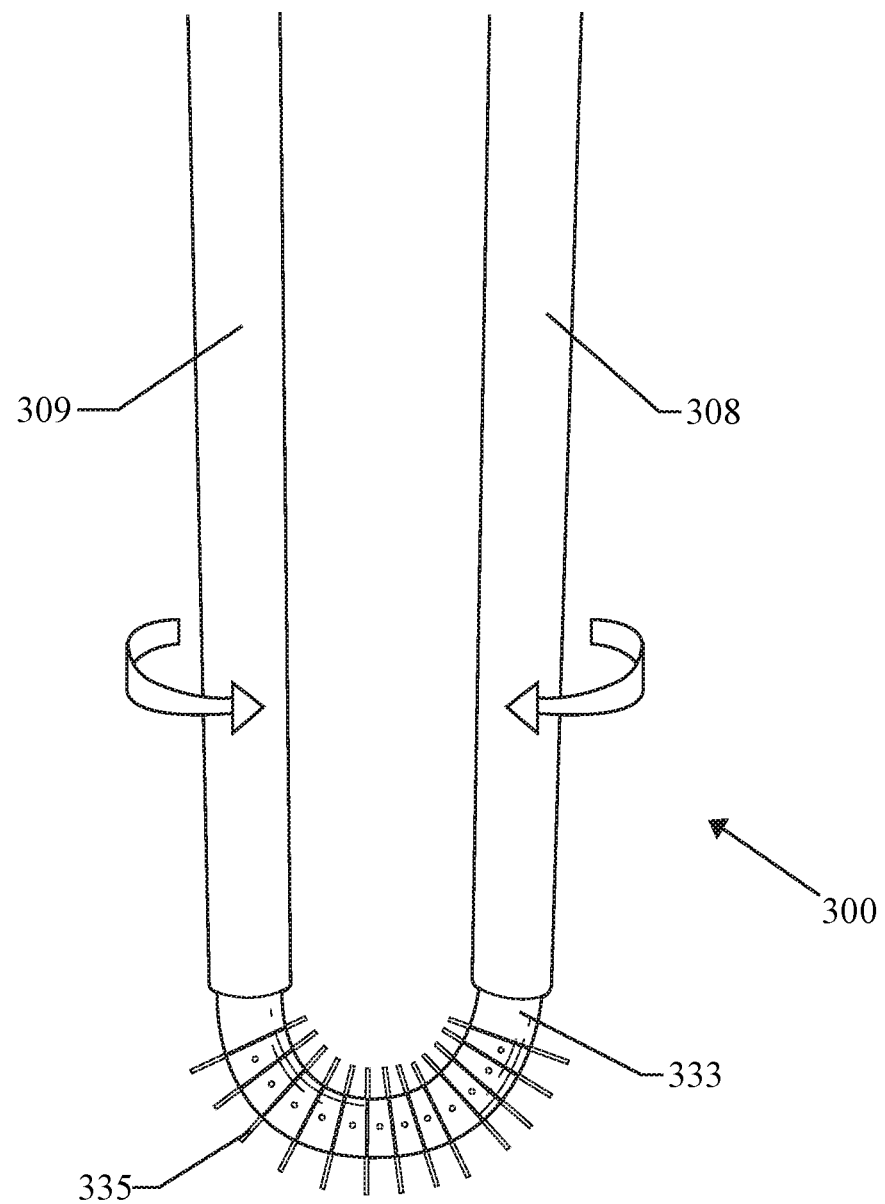
FIG. 3 is an illustration of a close-up view of one embodiment of a cutting tool showing the two rods and the cutter.

FIG. 3 is an illustration of a close-up view of one embodiment of a cutting tool showing the two rods and the cutter. FIG. 3 shows that the cutting tool has two rods 308, 309 that are configured to rotate in opposite directions 300. As shown, the distal ends of rods 308, 309 may have a flexible connector 333, such as a neoprene section, silicone, or tube that connects to the ends of rods 308, 309. Preferably, the connector 333 is securely connected to the rods 308, 309, such that when the rods 308, 309 turn in opposite directions the connector tube 333 spins at the same speed that the rods 308, 309 rotate. FIG. 3 shows that the connector 333 may have one or more pins 335 that are embedded in the connector 333 such that one or both ends of the pins 335 are sticking out of the connector. As such, when the connector 333 spins, the pins 335 spin as well and the connector 333 and pins 335 act as a cutter or cutting tip. Multiple pins 335 are shown in FIG. 3, which allows a relatively wide cutting area. The pins 335 may be made from hard stainless steel or a softer bendable wire. The embodiment shown in FIG. 3 might be useful for clearing away cartilage or scar tissue because of the wide cutting surface. In an alternate embodiment, the pins 335 may function to scrub and/or polish the surface of a solid surface, such as a bone, in order to clean the bone and allow for a better bone fusion.

The connector 333 may be made of other materials, such as high grade soft plastic, a flexible fiberglass, an expandable, sheathing, and flexible metal, or a flexible composite.

Figure 4:
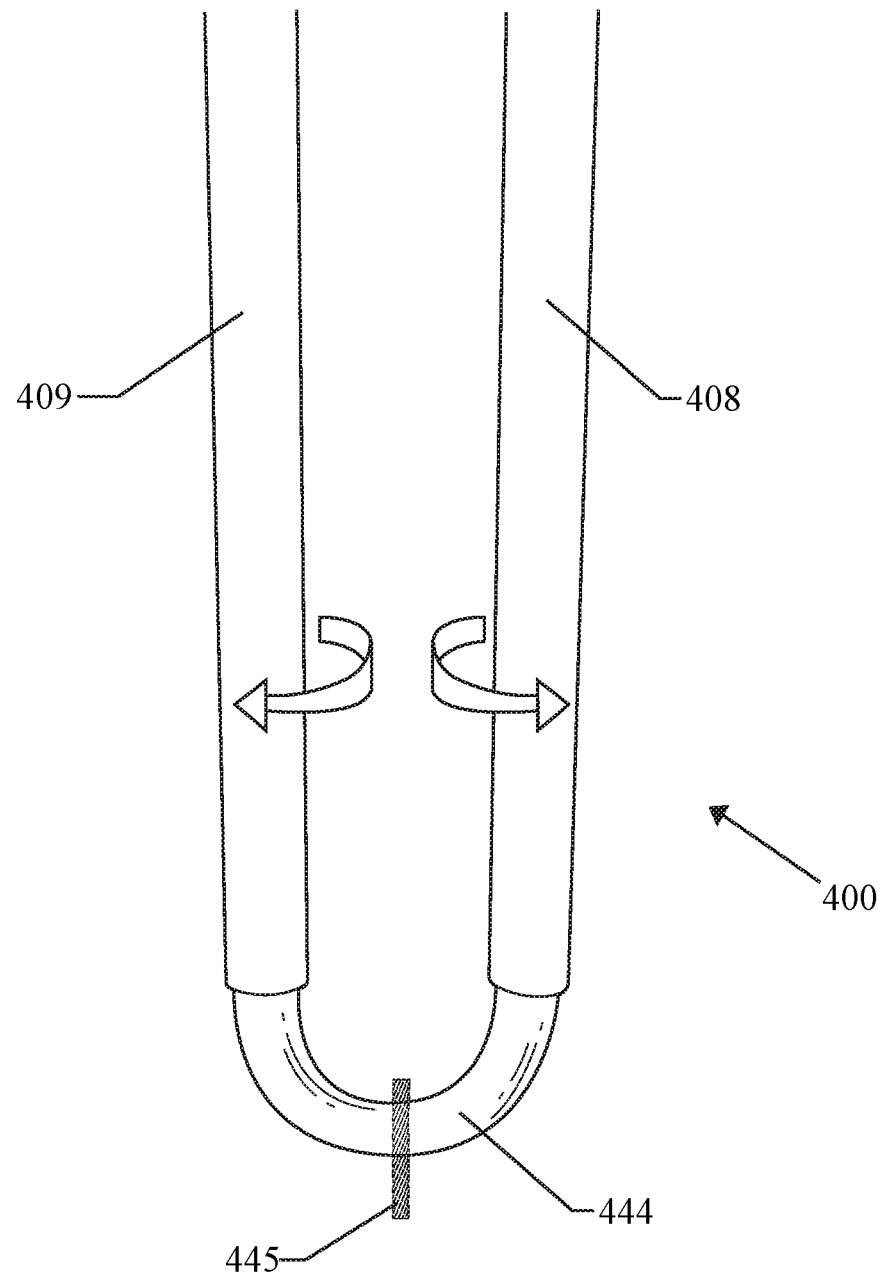
FIG. 4 is an illustration of a close-up view of another embodiment of a cutting tool showing the two rods and the cutter.

FIG. 4 is an illustration of a close-up view of another embodiment of a cutting tool showing the two rods and the cutter. FIG. 4 shows that the cutting tool has two rods 408, 409 that are configured to rotate in opposite directions 400. As shown, the distal ends of rods 408, 409 may have a flexible connector 444, such as a neoprene section or tube that connects to the ends of rods 408, 409. Preferably, the connector 444 is securely connected to the rods 408, 409, such that when the rods 408, 409 turn in opposite directions the connector tube 444 spins at the same speed that the rods 408, 409 rotate. FIG. 4 shows that the connector 444 may have a wire 445 that is embedded in, or held securely in place by, the connector 444 such that one or two ends of the wire 445 is sticking out of the connector. As such, when the connector 444 spins, the wire 445 spins as well and the connector 444 and wire 445 act as a cutter or cutting tip. A single wire 445 is shown in FIG. 4, which allows a relatively narrow cutting area that is only as wide as the wire 445. The wire 445 may be of varying hardness and may be interchangeable so that the best cutter may be selected by selecting the appropriate wire. Use of soft wires may prevent bone from being cut or damaged when the cutting tool is use, but still allow soft tissue to be cut. The narrow cutting area shown in FIG. 4 allows for precise cuts to be made. In an alternate embodiment, the rods 408, 409 may be flexible to allow for bending of the rods 408, 409 in order to increase access to hard to reach spaces. In another embodiment, the rods 408, 409 may comprise cutting and/or polishing pins.

The pins 335 and wire 445 may be referred to as the active cutting portion.

Figure 5:
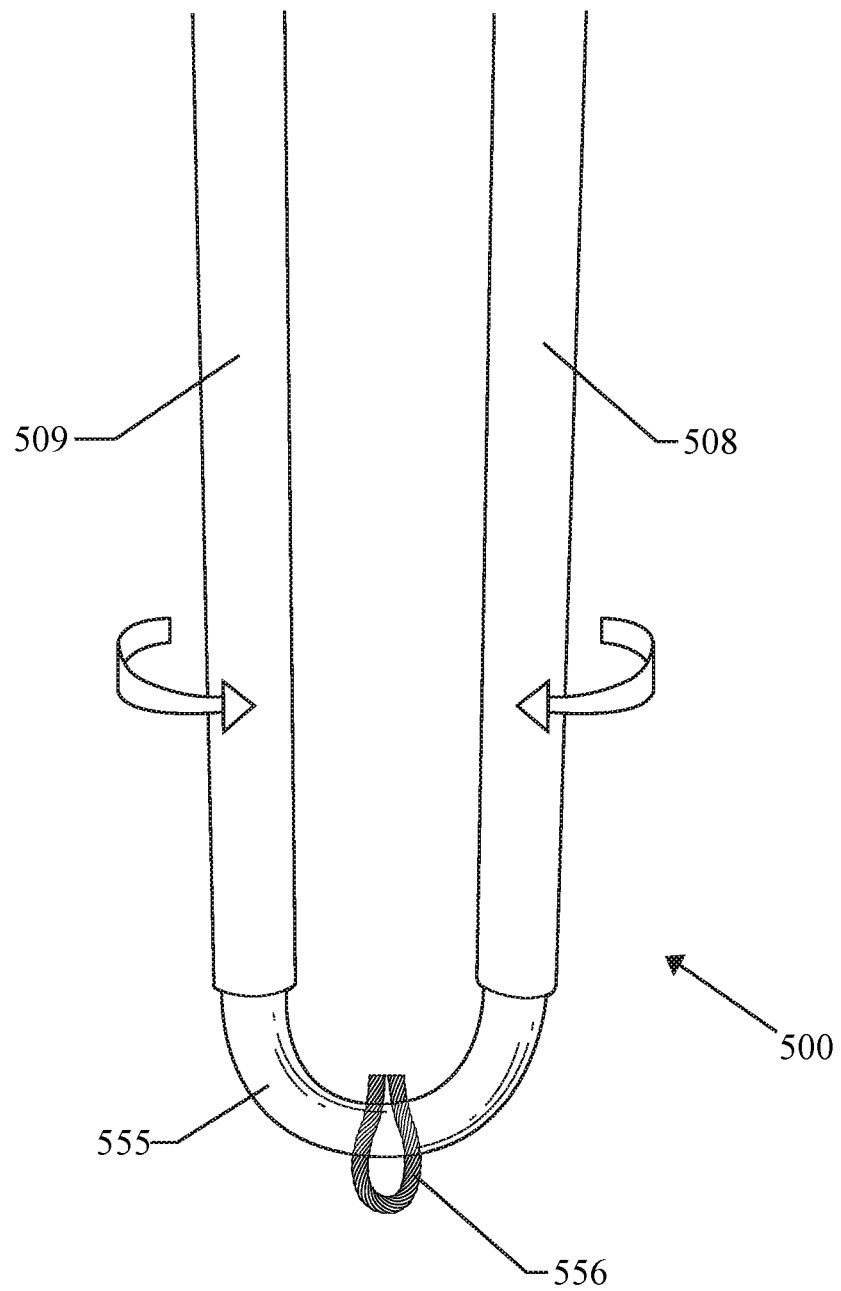
FIG. 5 is an illustration of a close-up view of another embodiment of a cutting tool showing the two rods and the cutter.

FIG. 5 is an illustration of a close-up view of another embodiment of a cutting tool showing the two rods and the cutter. FIG. 5 shows that the cutting tool has two rods 508, 509 that are configured to rotate in opposite directions 500. As shown, the distal ends of rods 508, 509 may have a flexible connector 555, such as a neoprene section or tube that connects to the ends of rods 508, 509. Preferably, the connector 555 is securely connected to the rods 508, 509, such that when the rods 508, 509 turn in opposite directions the connector tube 555 spins at the same speed that the rods 508, 509 rotate. FIG. 5 shows that the connector 555 may have a wire 556 that is embedded in, or held securely in place by, the connector 555 such that one or two ends of the wire 556 is sticking out of the connector. As such, when the connector 555 spins, the wire 556 spins as well and the connector 555 and wire 556 act as a cutter or cutting tip. A single loop wire 556 is shown in FIG. 5, which allows a wide, flat, and consistent cutting area. The wire 556 may be of varying hardness and may be interchangeable so that the best cutter may be selected by selecting the appropriate wire. Use of soft wires may prevent bone from being cut or damaged when the cutting tool is use, but still allow soft tissue to be cut. The narrow cutting area shown in FIG. 5 allows for precise cuts to be made.

Figure 6:
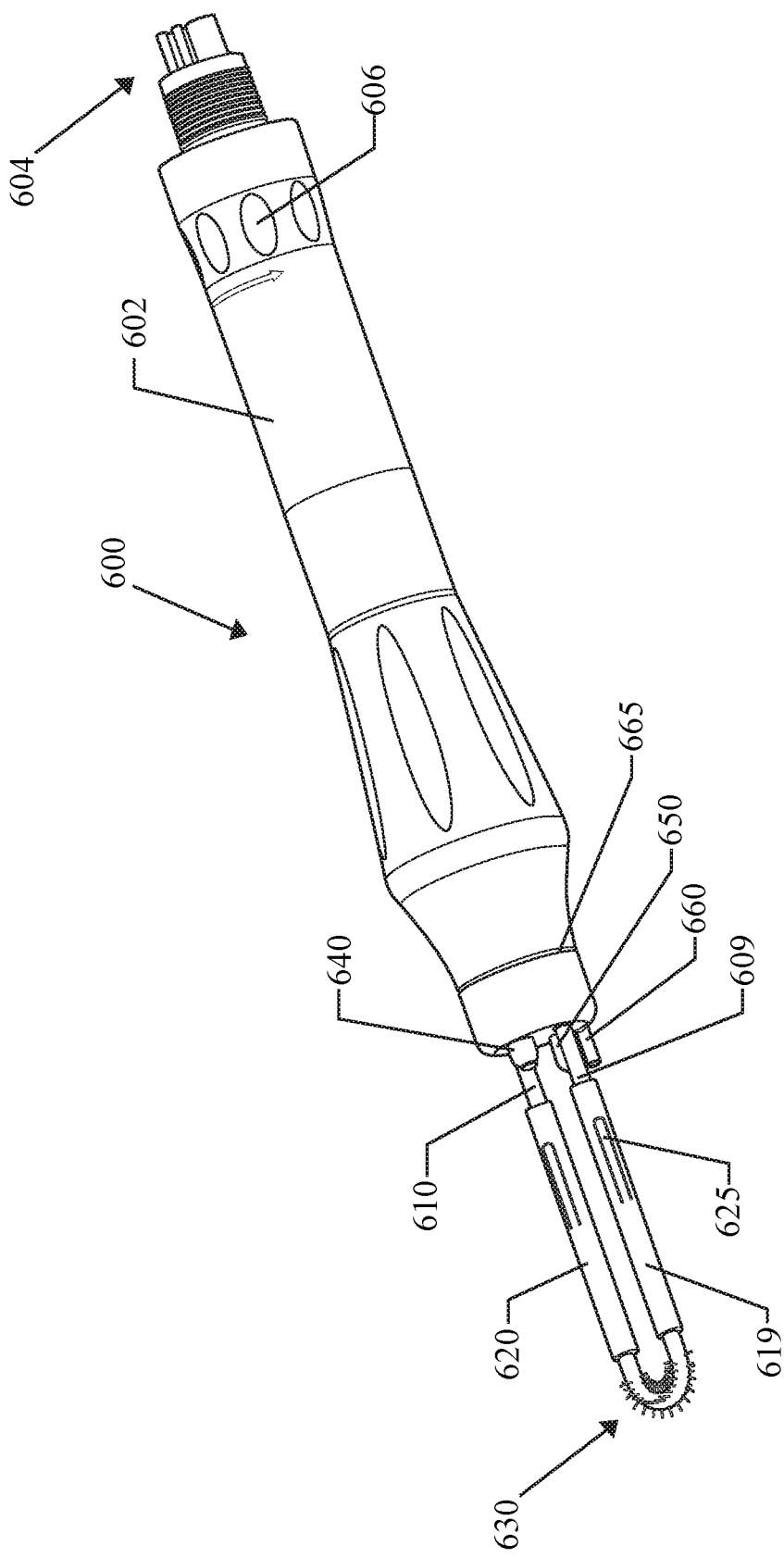
FIG. 6 is an illustration of a perspective side view of one embodiment of a cutting tool.

FIG. 6 is an illustration of a perspective side view of one embodiment of a cutting tool. FIG. 6 shows that the cutting tool 600 may comprise a housing 602, a motor, motor speed controller 606, rods 609, 610, cutter 630, rear coupling 604, rod tips 619, 620, LED/laser/light 640, camera 650, and rinse/suction 660. As shown the motor speed controller 606 may be a dial that both turns on/off the cutting tool and allows the user to adjust the speed. FIG. 6 shows that the rods 609, 610 may connect to rod tips 619, 620, which may removeably couple together via connector 625, which is shown as a living hinge, but may be any type of connector that allows the rods and tips to removably, but securely engage or connect. In another embodiment, the rods 609, 610 may be permanently attached to the rod tips 619, 620, or may be unitary portions thereof. The rod tips 619, 620 may be connected to, or may comprise, the cutter 630, which as shown is a flexible arched tip with embedded pins or wires. The LED/laser/light 640 may be an LED light, a laser, or another type of light source. The laser may point at the tissue portion that is about to be cut. The light may illuminate the area that is being cut. The camera 650 may allow the user to view the tissue being cut on an external monitor. The rinse/suction 660 may either provide suction to the area to remove fluid or debris, or it may rinse the area with a fluid (liquid or gas) that may wash or dry the tissue area. The cutting tool 600 may also comprise an attachment section 665, wherein the replaceable cutting tip 899 may attach at that portion.

Figure 7:
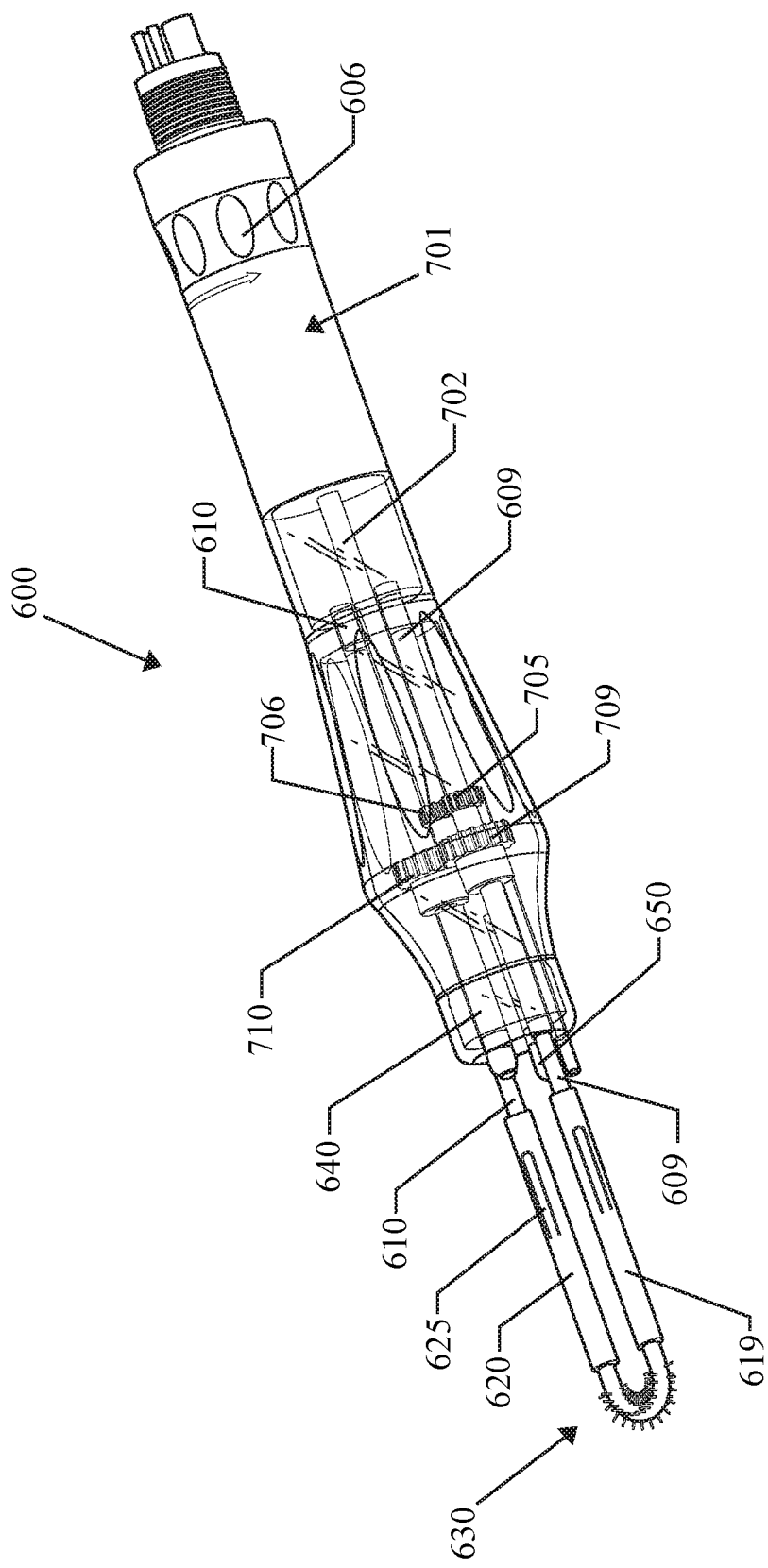
FIG. 7 is an illustration of a perspective side view of one embodiment of a cutting tool.

FIG. 7 is an illustration of a perspective side view of one embodiment of a cutting tool. FIG. 7 shows that the cutting tool 600 may comprise a housing 602, a motor 701, motor speed controller 606, rods 609, 610, cutter 630, rear coupling 604, rod tips 619, 620, LED/laser/light 640, camera 650, and rinse/suction 660. FIG. 7 also shows that the motor 701 may be connected to a drive shaft 702. The drive shaft 702 may comprise a rod engagement gear 706, which, as shown, may engage with rod gear 705. Rod gear 705 may be part of, or coupled to rod 609, such that when rod gear 705 is turned by the drive shaft 702, rod 609 is also turned. Rod gear 705 and/or rod 609 may further be engaged with or comprise first synchronization gear 709, which may engage with second synchronization gear 710. When the rod 609 and rod gear 705 turn, first synchronization gear 709 also turns, which causes the second synchronization gear 710 to turn in the opposite direction as first synchronization gear 709. Second synchronization gear 710 may be part of or may be coupled to rod 610, such that when second synchronization gear 710 turns, rod 610 turns as well. In this manner, rods 609, 610 turn in a synchronized manner in opposite directions. This may cause the rod tips 619, 620 to turn in opposite directions, which, in turn, causes the cutter 630 to spin. In one embodiment, the rods 609, 610 may be substantially parallel and identical. In an alternative embodiment, the rods 609, 610 may include a small bend or angle towards the rod tips 619, 620, which may cause the rods 609, 610 to impart a vibration to the cutter 630, which may in turn increase the cutting area and allow for a back and forth motion in the cutter 630, which may allow the cutter 630 to reach behind objects such as bone.

Figure 8:
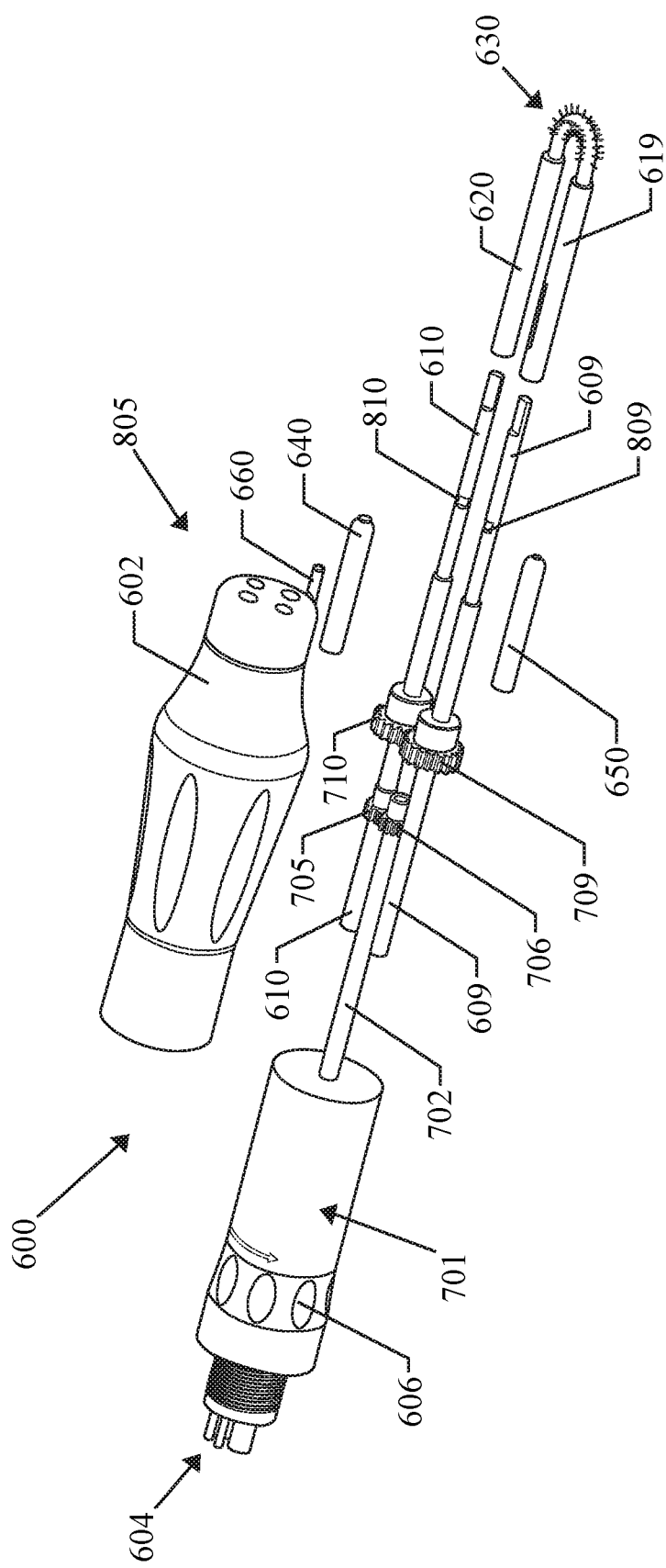
FIG. 8 is an illustration of an exploded view of one embodiment of a cutting tool.

FIG. 8 is an illustration of an exploded view of one embodiment of a cutting tool. FIG. 8 shows that the cutting tool 600 may comprise a housing 602, a motor 701, motor speed controller 606, rods 609, 610, cutter 630, rear coupling 604, rod tips 619, 620, LED/laser/light 640, camera 650, and rinse/suction 660. FIG. 8 also shows that the motor 701 may be connected to a drive shaft 702. The drive shaft 702 may comprise a rod engagement gear 706, which, as shown, may engage with rod gear 705. Rod gear 705 may be part of, or coupled to rod 609, such that when rod gear 705 is turned by the drive shaft 702, rod 609 is also turned. Rod gear 705 and/or rod 609 may further be engaged with or comprise first synchronization gear 709, which may engage with second synchronization gear 710. When the rod 609 and rod gear 705 turn, first synchronization gear 709 also turns, which causes the second synchronization gear 710 to turn in the opposite direction as first synchronization gear 709. Second synchronization gear 710 may be part of or may be coupled to rod 610, such that when second synchronization gear 710 turns, rod 610 turns as well. In this manner, rods 609, 610 turn in a synchronized manner in opposite directions. This causes the rod tips 619, 620 to turn in opposite directions, which, in turn, causes the cutter 630 to spin. FIG. 8 shows that the rod tips 619, 620 may be removeably connected to rods 609, 610. The rods 609, 610 may have notches 809, 810 that may engage with the connectors 625, 626 of the rod tips 619, 620.

FIG. 8 shows that the housing 602 may have a top portion 805 that have a plurality of apertures that allow the rods 609, 610, LED/laser/light 640, camera 650, and rinse/suction 660 to project out of the housing and to be supported. Preferably, the apertures of top portion 805 fit snugly around the parts that pass through them so that no fluids or debris enter the housing 602.

Figure 9:
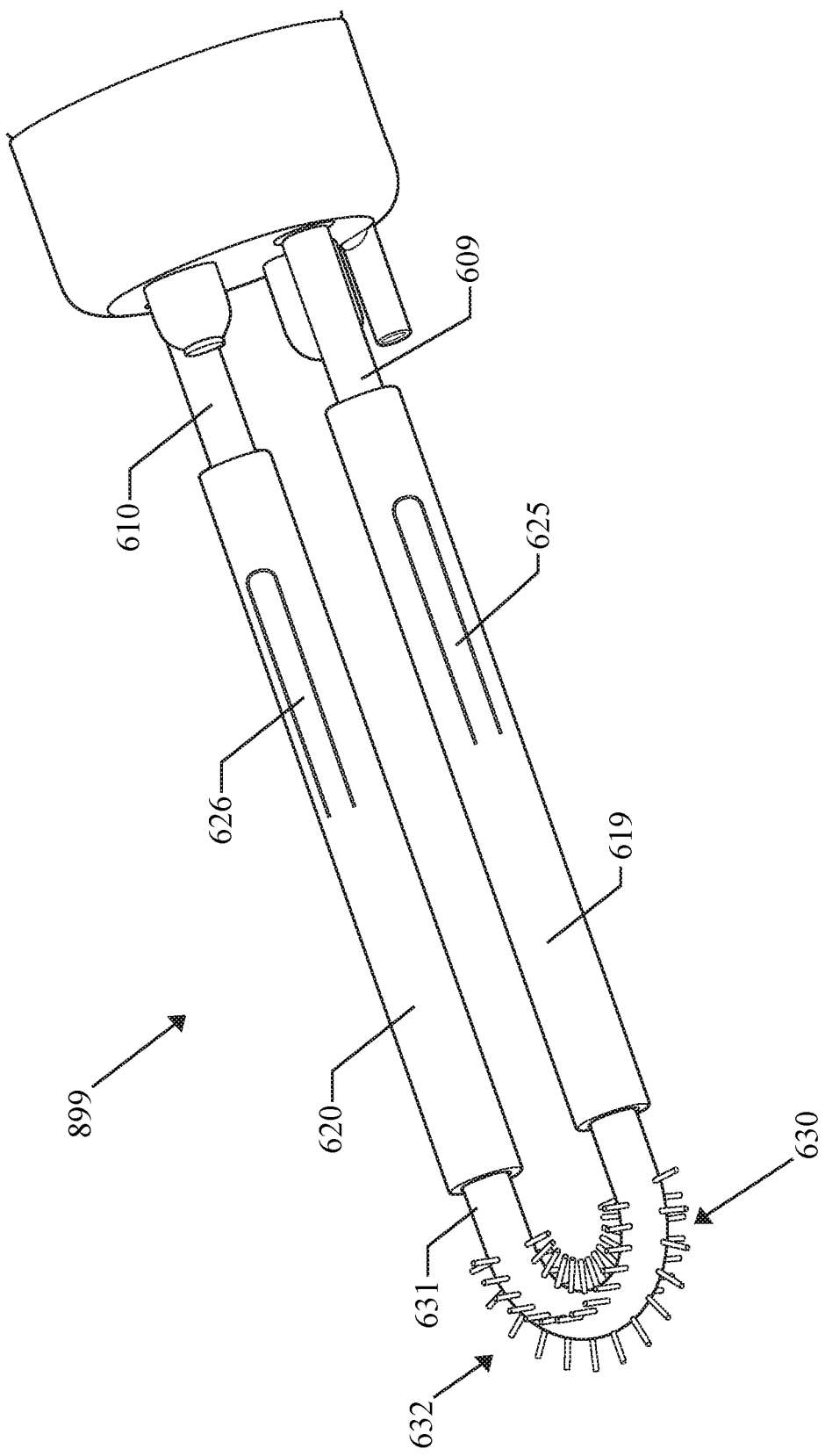
FIG. 9 is an illustration of a close up view of one embodiment of a cutting tool showing the cutter.

FIG. 9 is an illustration of a close up view of one embodiment of a cutting tool showing the cutter. FIG. 9 shows that the rod tips 619, 620 and the cutter 630 may comprise a single unitary part that acts as a replaceable cutting tip 899. The rod tips 619, 620 may be removeably connected to rods 609, 610. The rods 609, 610 may have notches 809, 810 (shown in FIG. 8) or some other engagement portion that may engage with the connectors 625, 626 of the rod tips 619, 620. FIG. 9 also shows that the cutter 630 may comprise a silicone rubber bent base 631, which may comprise or be engaged with pins 632. The harder the pins 632 are and the faster they rotate when the rods 609, 610 spin in opposite directions, the more cutting power cutter 630 has. The replaceable cutting tip 899 may be a sterile single use tip intended for use during a single surgery.

Figure 10:
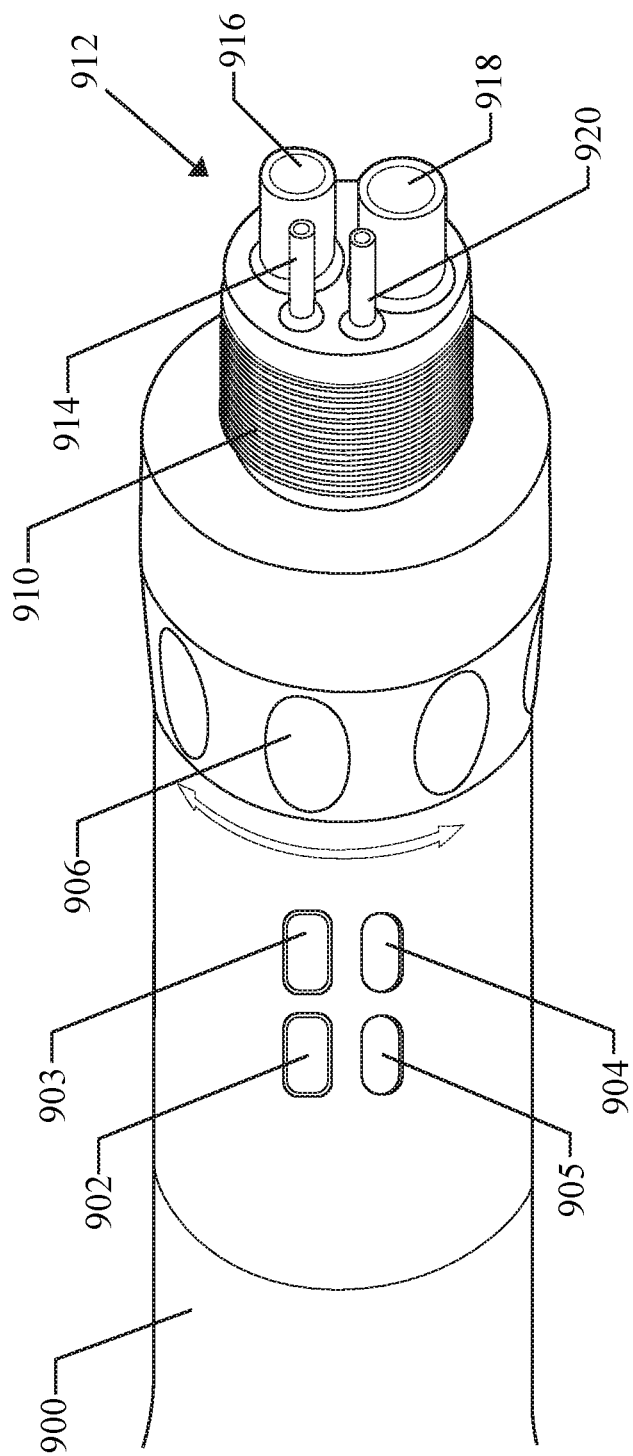
FIG. 10 is an illustration of a close up view of one embodiment of a cutting tool showing the rear coupling.

FIG. 10 is an illustration of a close up view of one embodiment of a cutting tool showing the rear coupling.

FIG. 10 shows that the cutting tool 900 may comprise user interfaces 902, 903, 904, 905 which may be on/off buttons that control the cutting tool 900, a suction, a rinse, a light, a LED light, a laser, or a camera. The cutting tool 900 may also have a speed controller 906, which allows the user to speed up or slow down the rotation of the cutter or cutting tip. The cutting tool 900 may have a rear coupling 912 that comprises engagement threads/grips 910 and engagements/apertures 914, 916, 918, 920. The engagements/apertures 914, 916, 918, 920 may allow wires and/or air tubes to pass through into the housing of the tool 900 so that the user may power the cutter, the lights, the rinse, the suction, the laser, and/or the camera.

Unless otherwise stated, all measurements, values, ratings, positions, magnitudes, sizes, locations, and other specifications, which set forth in this specification, including in the claims that follow, are approximate, not exact. They are intended to have a reasonable range, which is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description, which shows and describes the illustrative embodiments. As will be realized, these embodiments are capable of modifications in various obvious aspects, all without departing from the spirit and scope of the present disclosure. Accordingly, the detailed description is to be regarded as illustrative in nature and not restrictive. Also, although not explicitly recited, one or more additional embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing which has been stated or illustrated is intended or should be interpreted to cause a dedication of any component, step, feature, object, benefit, advantage, or equivalent to the public, regardless of whether it is or is not recited in the claims.

What is claimed is:

1. A cutting tool, comprising:
   a motor;
   two rods including, a first rod and a second rod;
   a synchronization gearing; and
   a cutter;
   wherein said motor turns said first rod in a first direction;
   wherein said synchronization gearing is operatively coupled to said first rod and said second rod, such that when said motor turns said first rod in said first direction, the second rod is turned in an opposite direction but at the same speed as the first rod;
   wherein said cutter is connected to both of said two rods, such that when said two rods spin in opposite directions said cutter rotates.

2. The cutting tool of claim 1, further comprising a drive shaft;
   wherein said synchronization gearing comprises a first synchronization gear and a second synchronization gear;
   wherein said motor is connected to and drives said drive shaft;
   wherein said first rod comprises a rod gear and is connected to said first synchronization gear;

wherein said second synchronization gear is connected to said second rod;

wherein said drive shaft comprises a rod engagement gear, which engages with said rod gear, such that when said drive shaft turns said first rod and said first synchronization gear turn;

wherein said first synchronization gear and said second synchronization gear are configured to engage, such that when said first rod turns, said second rod turns at the same speed in an opposite direction.

3. The cutting tool of claim 1, wherein said cutter comprises a flexible portion and an active cutting portion.

4. The cutting tool of claim 3, wherein said active cutting portion is a wire.

5. The cutting tool of claim 4, wherein said wire is not able to damage bone during operation of said cutting tool.

6. The cutting tool of claim 3, wherein said active cutting portion is a plurality of pins.

7. The cutting tool of claim 3, wherein said cutter further comprises two rod tips;
wherein said two rod tips are configured to removeably connect to said two rods, such that said cutter is removeably connected to said cutting tool.

8. The cutting tool of claim 1, further comprising at least one accessory selected from the group of accessories consisting of: a light; a LED light; a laser; a camera; a rinse; and a suction.

9. The cutting tool of claim 1, further comprising a speed controller;
wherein said speed controller is configured to adjust a speed of said cutting tool.

10. The cutting tool of claim 1, wherein the motor is selected from the group of motors consisting of an electric motor and a pneumatic motor.

11. A cutting tool, comprising:
a motor;
two rods including, a first rod and a second rod;
a synchronization gearing;
a drive shaft; and
a cutter;
wherein said synchronization gearing comprises a first synchronization gear and a second synchronization gear;
wherein said motor is connected to and drives said drive shaft;
wherein said first rod comprises a rod gear and is connected to said first synchronization gear;
wherein said second synchronization gear is connected to said second rod;
wherein said drive shaft comprises a rod engagement gear, which engages with said rod gear, such that when said drive shaft turns said first rod and said first synchronization gear turn;
wherein said first synchronization gear and said second synchronization gear are configured to engage, such that when said first rod turns in a first direction, said second rod turns at the same speed in an opposite direction; and
wherein said cutter is connected to both of said two rods, such that when said two rods spin in opposite directions said cutter rotates.

12. The cutting tool of claim 11, wherein said cutter comprises a flexible portion and an active cutting portion.

13. The cutting tool of claim 12, wherein said cutter further comprises two rod tips;
wherein said two rod tips are configured to removeably connect to said two rods, such that said cutter is removeably connected to said cutting tool.

14. The cutting tool of claim 12, wherein said active cutting portion is selected from the group of active cutting portions consisting of: a wire; a pin; and a plurality of pins.

15. The cutting tool of claim 12, further comprising at least one accessory selected from the group of accessories consisting of: a light; a LED light; a laser; a camera; a rinse; and a suction.

16. The cutting tool of claim 12, further comprising a speed controller;
wherein said speed controller is configured to adjust a speed of said cutting tool.

17. A cutting tool, comprising:
a motor;
two rods including, a first rod and a second rod;
a synchronization gearing;
a drive shaft; and
a cutter;
wherein said synchronization gearing comprises a first synchronization gear and a second synchronization gear;
wherein said motor is connected to and drives said drive shaft;
wherein said first rod comprises a rod gear and is connected to said first synchronization gear;
wherein said second synchronization gear is connected to said second rod;
wherein said drive shaft comprises a rod engagement gear, which engages with said rod gear, such that when said drive shaft turns said first rod and said first synchronization gear turn;
wherein said first synchronization gear and said second synchronization gear are configured to engage, such that when said first rod turns in a first direction, said second rod turns at the same speed in an opposite direction; and
wherein said cutter is connected to both of said two rods, such that when said two rods spin in opposite directions said cutter rotates;
wherein said cutter comprises a flexible portion, an active cutting portion, and two rod tips;
wherein said two rod tips are configured to removeably connect to said two rods, such that said cutter is removeably connected to said cutting tool.

18. The cutting tool of claim 17, wherein said active cutting portion is selected from the group of active cutting portions consisting of: a wire; a pin; and a plurality of pins.

19. The cutting tool of claim 18, further comprising at least one accessory selected from the group of accessories consisting of: a light; a LED light; a laser; a camera; a rinse; and a suction.

20. The cutting tool of claim 19, further comprising a speed controller;
wherein said speed controller is configured to adjust a speed of said cutting tool.

* * * * *